US008556987B2

(12) United States Patent
Hunter et al.

(10) Patent No.: US 8,556,987 B2
(45) Date of Patent: *Oct. 15, 2013

(54) METHOD OF PROVIDING A ZIRCONIUM SURFACE AND RESULTING PRODUCT

(75) Inventors: Gordon Hunter, Germantown, TN (US); Shilesh C. Jani, Germantown, TN (US); Vivek Pawar, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 40 days.

This patent is subject to a terminal disclaimer.

(21) Appl. No.: 12/971,933

(22) Filed: Dec. 17, 2010

(65) Prior Publication Data
US 2011/0139312 A1 Jun. 16, 2011

Related U.S. Application Data

(60) Continuation of application No. 12/277,013, filed on Nov. 24, 2008, now Pat. No. 7,896,926, which is a division of application No. 10/942,464, filed on Sep. 16, 2004, now Pat. No. 7,473,278.

(51) Int. Cl.
*A61F 2/28* (2006.01)
(52) U.S. Cl.
USPC ...................................... 623/23.56
(58) Field of Classification Search
None
See application file for complete search history.

(56) References Cited

U.S. PATENT DOCUMENTS

| 2,987,352 | A | 6/1961 | Watson |
| 3,165,885 | A | 1/1965 | Tenney et al. |
| 3,287,111 | A | 11/1966 | Klepfer |
| 3,615,885 | A | 10/1971 | Watson et al. |
| 3,715,265 | A | * 2/1973 | Allen et al. ................... 428/143 |
| 4,145,764 | A | 3/1979 | Suzuki et al. |
| 4,160,680 | A | 7/1979 | Novy et al. |
| 4,238,251 | A | 12/1980 | Williams et al. |
| 4,272,855 | A | 6/1981 | Frey et al. |
| 4,381,716 | A | 5/1983 | Hastings et al. |
| 4,644,942 | A | 2/1987 | Sump |

(Continued)

FOREIGN PATENT DOCUMENTS

| DE | 19815598 | 10/1999 |
| EP | 0410711 | 1/1991 |

(Continued)

OTHER PUBLICATIONS

Dhawan et al., "Study of Oxidental Behaviour of Zr-based bulk amorphous ally Zr65Cu17-5Ni10Al7-5 by thermogravimetric analyser," Bull. Mater. Sci., vol. 24(3): 281-283, Jun. 2001 © Indian Academy of Sciences.

(Continued)

*Primary Examiner* — Alvin J. Stewart
(74) *Attorney, Agent, or Firm* — David A. Chambers

(57) ABSTRACT

A coating of blue-black or black zirconium of uniform and controlled thickness on a zirconium or zirconium alloy material is accomplished through the treatment of an amorphous zirconium or zirconium alloy substrate, which may have an altered surface roughness. The treatment of amorphous zirconium or zirconium alloy substrates includes oxidation of the substrates. A zirconium coating of uniform and controlled thickness is especially useful in various applications because the uniformly thick zirconium surface of controlled depth provide a barrier against implant corrosion caused by ionization of the metal substrates.

20 Claims, 4 Drawing Sheets

(56) References Cited

U.S. PATENT DOCUMENTS

| | | | |
|---|---|---|---|
| 4,662,288 A | 5/1987 | Hastings et al. | |
| 4,671,824 A | 6/1987 | Haygarth | |
| 4,673,409 A | 6/1987 | Van Kampen | |
| 4,746,532 A | 5/1988 | Suzuki et al. | |
| 4,747,915 A | 5/1988 | Pagani | |
| 4,860,757 A | 8/1989 | Lynch et al. | |
| 4,865,603 A | 9/1989 | Noiles | |
| 4,946,665 A * | 8/1990 | Recasens et al. | 423/608 |
| 5,017,830 A * | 5/1991 | Koike | 313/402 |
| 5,037,438 A | 8/1991 | Davidson | |
| 5,149,510 A * | 9/1992 | Recasens et al. | 423/84 |
| 5,152,794 A | 10/1992 | Davidson | |
| 5,169,597 A | 12/1992 | Davidson et al. | |
| 5,180,394 A | 1/1993 | Davidson | |
| 5,211,663 A | 5/1993 | Kovacs et al. | |
| 5,258,098 A | 11/1993 | Wagner et al. | |
| 5,282,861 A | 2/1994 | Kaplan | |
| 5,316,594 A | 5/1994 | Kemp | |
| 5,354,390 A | 10/1994 | Haszmann et al. | |
| 5,360,448 A | 11/1994 | Thramann | |
| 5,370,694 A | 12/1994 | Davidson | |
| 5,372,660 A | 12/1994 | Davidson et al. | |
| 5,383,934 A | 1/1995 | Armini et al. | |
| 5,399,207 A | 3/1995 | Kemp | |
| 5,405,394 A * | 4/1995 | Davidson | 623/18.11 |
| 5,415,704 A | 5/1995 | Davidson | |
| 5,456,723 A | 10/1995 | Steinemann et al. | |
| 5,496,359 A * | 3/1996 | Davidson | 607/115 |
| 5,507,815 A | 4/1996 | Wagner et al. | |
| 5,509,933 A | 4/1996 | Davidson et al. | |
| 5,549,700 A | 8/1996 | Graham et al. | |
| 5,562,730 A | 10/1996 | Davidson | |
| 5,571,017 A | 11/1996 | Niznick | |
| 5,571,139 A | 11/1996 | Jenkins | |
| 5,588,443 A * | 12/1996 | Davidson | 600/585 |
| 5,611,347 A * | 3/1997 | Davidson | 600/510 |
| 5,628,790 A * | 5/1997 | Davidson et al. | 623/2.36 |
| 5,632,779 A * | 5/1997 | Davidson | 623/1.51 |
| 5,647,858 A * | 7/1997 | Davidson | 604/264 |
| 5,649,951 A * | 7/1997 | Davidson | 606/198 |
| 5,716,400 A | 2/1998 | Davidson | |
| 5,782,910 A | 7/1998 | Davidson | |
| 5,830,396 A | 11/1998 | Higgins et al. | |
| 5,840,610 A | 11/1998 | Gilmer et al. | |
| 5,843,289 A | 12/1998 | Lee et al. | |
| 5,868,879 A | 2/1999 | Amick et al. | |
| 5,922,029 A | 7/1999 | Wagner et al. | |
| 5,933,167 A | 8/1999 | Shimada et al. | |
| 6,043,437 A | 3/2000 | Schulman et al. | |
| 6,059,830 A | 5/2000 | Lippincott et al. | |
| 6,063,442 A | 5/2000 | Cohen et al. | |
| 6,087,553 A | 7/2000 | Cohen et al. | |
| 6,146,686 A | 11/2000 | Leitao | |
| 6,193,762 B1 | 2/2001 | Wagner et al. | |
| 6,207,218 B1 | 3/2001 | Layrolle et al. | |
| 6,238,491 B1 | 5/2001 | Davidson et al. | |
| 6,294,274 B1 * | 9/2001 | Kawazoe et al. | 428/697 |
| 6,312,472 B1 | 11/2001 | Hall et al. | |
| 6,395,327 B1 | 5/2002 | Shetty | |
| 6,446,558 B1 | 9/2002 | Peker et al. | |
| 6,447,550 B1 | 9/2002 | Hunter et al. | |
| 6,472,122 B1 | 10/2002 | Schulman et al. | |
| 6,554,793 B1 | 4/2003 | Pauker et al. | |
| 6,585,772 B2 | 7/2003 | Hunter et al. | |
| 6,599,322 B1 | 7/2003 | Amrich et al. | |
| 6,652,586 B2 | 11/2003 | Hunter et al. | |
| 6,682,611 B2 | 1/2004 | Zhang et al. | |
| 6,726,725 B2 | 4/2004 | Hunter et al. | |
| 6,771,490 B2 | 8/2004 | Peker et al. | |
| 6,784,508 B2 | 8/2004 | Tsunashima et al. | |
| 6,791,649 B1 * | 9/2004 | Nakamura et al. | 349/137 |
| 6,818,078 B2 | 11/2004 | Kim et al. | |
| 6,833,197 B1 | 12/2004 | Dong et al. | |
| 6,843,496 B2 | 1/2005 | Peker et al. | |
| 6,875,293 B2 | 4/2005 | Peker | |
| 6,881,229 B2 | 4/2005 | Khandkar et al. | |
| 6,887,586 B2 | 5/2005 | Peker et al. | |
| 6,913,546 B2 * | 7/2005 | Kakiuchi | 473/345 |
| 6,921,702 B2 | 7/2005 | Ahn et al. | |
| 6,960,328 B2 * | 11/2005 | Bortun et al. | 423/139 |
| 6,974,625 B2 | 12/2005 | Hunter et al. | |
| 7,008,490 B2 | 3/2006 | Peker | |
| 7,017,645 B2 | 3/2006 | Johnson et al. | |
| 7,048,767 B2 | 5/2006 | Namavar | |
| 7,070,623 B2 | 7/2006 | Hunter et al. | |
| 7,086,963 B1 * | 8/2006 | Onuki et al. | 473/342 |
| 7,157,158 B2 | 1/2007 | Collier et al. | |
| 7,235,129 B2 * | 6/2007 | Chen et al. | 117/84 |
| 7,252,767 B2 * | 8/2007 | Bortun et al. | 210/660 |
| 7,258,810 B2 | 8/2007 | Hunter et al. | |
| 7,293,599 B2 | 11/2007 | Peker et al. | |
| 7,306,994 B2 | 12/2007 | Tsunashima et al. | |
| 7,368,023 B2 * | 5/2008 | Chang et al. | 148/403 |
| 7,473,278 B2 * | 1/2009 | Hunter et al. | 623/23.39 |
| 7,500,987 B2 | 3/2009 | Bassler et al. | |
| 7,550,209 B2 | 6/2009 | Pawar et al. | |
| 7,582,117 B2 | 9/2009 | Hunter et al. | |
| 7,648,735 B2 | 1/2010 | Hunter et al. | |
| 7,704,867 B2 | 4/2010 | Kim et al. | |
| 7,896,926 B2 * | 3/2011 | Hunter et al. | 623/23.56 |
| 7,923,067 B2 * | 4/2011 | Muramatsu et al. | 427/215 |
| 7,968,209 B2 | 6/2011 | Pawar et al. | |
| 2001/0019745 A1 | 9/2001 | Beele et al. | |
| 2001/0023120 A1 | 9/2001 | Tsunashima et al. | |
| 2002/0042656 A1 | 4/2002 | Hunter et al. | |
| 2003/0044301 A1 | 3/2003 | Lefebvre et al. | |
| 2003/0125808 A1 | 7/2003 | Hunter et al. | |
| 2003/0153979 A1 | 8/2003 | Hughes et al. | |
| 2003/0153981 A1 | 8/2003 | Wang et al. | |
| 2003/0202932 A1 * | 10/2003 | Elder et al. | 423/598 |
| 2003/0207727 A1 * | 11/2003 | Kakiuchi | 473/345 |
| 2003/0220699 A1 | 11/2003 | Hunter et al. | |
| 2004/0002766 A1 | 1/2004 | Hunter et al. | |
| 2004/0007532 A1 * | 1/2004 | Bortun et al. | 210/660 |
| 2004/0023461 A1 | 2/2004 | Ahn et al. | |
| 2004/0034432 A1 | 2/2004 | Hughes et al. | |
| 2004/0122524 A1 | 6/2004 | Hunter et al. | |
| 2004/0224182 A1 * | 11/2004 | Lazarev | 428/690 |
| 2004/0232406 A1 * | 11/2004 | Weiss et al. | 257/35 |
| 2005/0006675 A1 | 1/2005 | Tsunashima et al. | |
| 2005/0009693 A1 * | 1/2005 | Woodhead | 502/302 |
| 2005/0023603 A1 * | 2/2005 | Eldridge et al. | 257/315 |
| 2005/0033442 A1 | 2/2005 | Fisher et al. | |
| 2005/0079200 A1 * | 4/2005 | Rathenow et al. | 424/423 |
| 2005/0083047 A1 * | 4/2005 | Lee et al. | 324/210 |
| 2005/0129949 A1 | 6/2005 | Hunter et al. | |
| 2005/0164045 A1 * | 7/2005 | Rothbrust et al. | 428/701 |
| 2005/0287348 A1 * | 12/2005 | Faler et al. | 428/315.5 |
| 2006/0020346 A1 | 1/2006 | Hunter et al. | |
| 2006/0030663 A1 * | 2/2006 | Andre et al. | 524/588 |
| 2006/0052880 A1 | 3/2006 | Brosnahan et al. | |
| 2006/0058888 A1 | 3/2006 | Hunter et al. | |
| 2006/0169364 A1 | 8/2006 | Trotzschel et al. | |
| 2006/0259150 A1 | 11/2006 | Hunter et al. | |
| 2007/0016163 A1 | 1/2007 | Santini et al. | |
| 2007/0023388 A1 * | 2/2007 | Nair et al. | 216/13 |
| 2007/0032877 A1 | 2/2007 | Whiteside | |
| 2007/0137734 A1 | 6/2007 | Pawar et al. | |
| 2008/0038460 A1 * | 2/2008 | Muramatsu et al. | 427/227 |
| 2008/0047931 A1 | 2/2008 | Fesmire et al. | |
| 2008/0102616 A1 | 5/2008 | Tsunashima et al. | |
| 2008/0156600 A1 * | 7/2008 | Eastham | 188/250 B |
| 2008/0196985 A1 * | 8/2008 | Meckel | 188/218 XL |
| 2008/0281429 A1 | 11/2008 | Pawar et al. | |
| 2009/0012611 A1 | 1/2009 | Brosnahan et al. | |
| 2009/0074836 A1 | 3/2009 | Pawar et al. | |
| 2009/0112331 A1 | 4/2009 | Hunter et al. | |
| 2009/0305882 A1 * | 12/2009 | Dahar et al. | 502/303 |
| 2010/0166548 A1 | 7/2010 | Sayano et al. | |
| 2010/0174383 A1 | 7/2010 | Pawar et al. | |
| 2011/0015756 A1 | 1/2011 | Pawar et al. | |

(56) References Cited

U.S. PATENT DOCUMENTS

FOREIGN PATENT DOCUMENTS

| EP | 0555038 | 8/1993 |
|---|---|---|
| EP | 0 608 997 | 8/1994 |
| EP | 2077124 | 7/2009 |
| JP | 07-173587 | 7/1995 |
| JP | 2001518827 | 10/2001 |
| JP | 2004089580 | 3/2004 |
| WO | WO-9402083 | 2/1994 |
| WO | WO-9616611 | 6/1996 |
| WO | WO-98/42390 | 10/1998 |
| WO | WO-9904055 | 1/1999 |
| WO | WO-01/54565 | 8/2001 |
| WO | WO-03/008657 | 1/2003 |
| WO | WO-2005/037468 | 4/2005 |

OTHER PUBLICATIONS

Horton et al., "Biomedical Potential of a Zirconium-Based BulkMetallic Glass," found at: http://www.ornl.gov/~webworks/cppr/y2001/pres/116372.pdf; Article No. 116372; 2003.

International Preliminary Report on Patentability issued Mar. 20, 2007, during the prosecution of International Application No. PCT/US2005/032919. Published Mar. 20, 2007.

International Search Report issued Mar. 21, 2006, during the prosecution of International Application No. PCT/US2005/032919. Published May 4, 2006.

Telford et al., "The case for bulk metallic glass," Materials Today, vol. 7, Issue 3, Mar. 2004, pp. 36-43.

Triwikantoro et al., "Oxidation of Zr-based metallic glasses in air," Journal of Non-Crystalline Solids, vol. 250-252, pp. 719-723; 1999.

Written Opinion issued Mar. 21, 2006, during the prosecution of International Application No. PCT/US2005/032919. Published Mar. 16, 2007.

European Examination Report in connection with Application No. 05 797 523.7-1215. Published Aug. 1, 2011.

Office Action in Foreign Proceedings JP2007-532456, dated Sep. 6, 2011 (english translation).

Office Action in Foreign Proceedings CA2,579,108, dated Oct. 12, 2011.

Gordon Hunter et al., Decision on Appeal: Appeal No. 2006-3075; U.S. Appl. No. 10/313,205; 9 pages; Feb. 28, 2007.

Appeal Brief filed during the prosecution of U.S. Appl. No. 10/313,205 with Appendices A; B; C1-C8; and D1-D7; filed Jan. 12, 2006.

D'Lima, Darryl D., M.D., et al., Bone Response to Implant Surface Morphology, The Journal of Arthroplasty, vol. 13, No. 8, pp. 928-934 (1998).

Wong, M., et al., Effect of surface topology on the osseointegration of implant materials in trabecular bone, Journal of Biomedical Materials Research, vol. 29, 1567-1575 (1995).

International Search Report dated Apr. 10, 2003.

Information Disclosure Statement by Applicant, U.S. Appl. No. 11/558,756, filed Jan. 30, 2007.

Supplemental Information Disclosure Statement by Applicant, U.S. Appl. No. 11/558,756, filed Dec. 18, 2007.

Second Supplemental Information Disclosure Statement by Applicant, U.S. Appl. No. 11/558,756, filed Aug. 29, 2008.

Revised Second Supplemental Information Disclosure Statement by Applicant, U.S. Appl. No. 11/558,756, filed Sep. 2, 2008.

Information Disclosure Statemenet by Applicant filed for U.S. Appl. No. 12/127,413 on May 27, 2008.

Information Disclosure Statement by Applicant filed for U.S. Appl. No. 12/244,492 on Jan. 23, 2009.

Information Disclosure Statemenet by Applicant filed for U.S. Appl. No. 12/244,492 on Aug. 9, 2010.

D.M. Brunette, P. Tengvall, M. Textor, and P. Thomsen, "Titanium in Medicine," Properties and Biological Significance of Natural Oxide Films on Titanium and Its Alloys, (Springer, Berlin, Germany, 2001), pp. 172-174 and 177.

Cox, B., "A mechanism for hydrogen uptake process in zirconium alloys", Journal of Nuclear Materials, 264 (1999) pp. 283-294.

J.D. Ehrman et al., "Micrrobial adhesion to zirconium alloys", Colloids and Surfaces B: Biointerfafces, 50 (2006) pp. 152-159.

Easterday, C.L., Ashtabula, Ohio, "Zirconium Analysis by Production Control Quantometer" Analytical Chemistry (U.S.) Formerly Ind. Eng. Chem., Anal. Ed.; vol. 31, No. 11, pp. 1867-1868, Nov. 1, 1959.

Hobbs et al., "Oxidation Microstructures and Interfaces in the Oxidized Zirconium Knee", *International Journal of Applied Ceramic Technology*, 2005, 221-246, vol. 2(3).

Long et al., "Nano-Hardness Measurements of Oxidized Zr-2.5Nb and Various Orthopaedic Materials", *24th Annual Meeting of the Society for Biomaterials*, Apr. 22-26, 1998, San Diego, California, USA.

Sprague et al., "mechanical Behavior of Zirconia, Alumina, and Oxidizen, Zirconium Modular Heads", *ISTA*, 2003, vol. 2.

Takamura, "Surface Hardening of Titanium by Oxygen", Trans. JIM, 1962, 10-14, vol. 3.

Treco, "Solution and Diffusion of Corrosion Oxide Film in Zircaloy", J. Electrochem. Soc., 1962, 208-211, vol. 109.

Application Examiners Report of Canadian Application 2,579,108 Issued Aug. 7, 2012, 2 pages.

\* cited by examiner

METHOD OF PROVIDING A ZIRCONIUM SURFACE AND RESULTING PRODUCT

CROSS-REFERENCE TO RELATED APPLICATIONS

The present application is a Continuation Application of U.S. application Ser. No. 12/277,013, which was filed on Nov. 24, 2008, entitled METHOD OF SURFACE OXIDIZING ZIRCONIUM AND ZIRCONIUM ALLOYS AND RESULTING PRODUCT and claims priority to U.S. application Ser. No. 10/942,464, which was filed on Sep. 16, 2004, entitled METHOD OF SURFACE OXIDIZING ZIRCONIUM AND ZIRCONIUM ALLOYS AND RESULTING PRODUCT, the disclosures of which are incorporated by reference herein in their entirety.

BACKGROUND OF THE INVENTION

This invention relates to metallic implants with load bearing surfaces coated with a thin, dense, low friction, highly wear-resistant, uniformly thick coating of oxidized zirconium.

The invention also relates to uniformly thick oxidized zirconium coatings on the non-load bearing surfaces of an orthopedic implant where the oxidized zirconium provides a barrier between the metallic prosthesis and body tissue thereby preventing the release of metal ions and corrosion of the implant. The invention further relates to a method of producing a uniformly thick oxidized zirconium layer by using an amorphous zirconium or zirconium alloy substrate with an altered surface roughness prior to formation of the oxide layer.

The excellent corrosion resistance of zirconium has been known for many years. Zirconium displays excellent corrosion resistance in many aqueous and non-aqueous media and for this reason has seen an increased use in the chemical process industry and in medical applications. A limitation to the wide application of zirconium in these areas is its relatively low resistance to abrasion and its tendency to gall. This relatively low resistance to abrasion and the tendency to gall is also demonstrated in zirconium alloys.

Orthopaedic implant materials must combine high strength, corrosion resistance and tissue compatibility. The longevity of the implant is of prime importance especially if the recipient of the implant is relatively young because it is desirable that the implant function for the complete lifetime of a patient. Of the conventional materials typically used to fabricate orthopaedic implants, each has its comparative advantages and disadvantages. In the case of metallic materials, because certain metal alloys have the required mechanical strength and biocompatibility without a high risk of brittle fracture, they are ideal candidates for the fabrication of prostheses. These alloys include 316L stainless steel, chrome-cobalt-molybdenum alloys and, more recently, titanium alloys which have proven to be the most suitable materials for the fabrication of load-bearing prostheses. However, metallic materials also have disadvantages. They are often not completely inert in the body. Body fluids act upon the metals causing them to slowly corrode by an ionizing process that thereby releases metal ions into the body. Metal ion release from the prosthesis is also related to the rate of wear of load bearing surfaces because the passive oxide film, which is formed on the surface, is constantly removed. The repassivation process constantly releases metal ions during the ionizing process. Furthermore, the presence of third-body wear (cement or bone debris) accelerates this process and microfretted metal particles increase friction against opposing surfaces. Surface hardness is not ideal in most metallic materials, resulting in scratching and microfretting. Other common materials have, other advantages and disadvantages. Ceramics, for examples, have very hard surfaces which resist scratching and microfretting, however, they are more brittle than metals and generally have inferior thermal properties.

In addition, the application of ceramic coating to metal substrates often results in non-uniform, poorly adhering coatings which tend to crack due to the differences in elastic modulus or thermal expansion between the ceramic and underlying metal substrate. Furthermore, such coatings tend to be relatively thick (50-300 microns) and since the bond between the metal and the ceramic coating is often weak, there is the risk of galling or separation of ceramic coatings.

The use of oxidized zirconium surfaces in orthopaedic implants represented an advance in that it allowed one to realize the advantages of metallic materials and ceramics while minimizing the disadvantages of both. Previous attempts have been made to produce oxidized zirconium coatings on zirconium parts for the purpose of increasing their abrasion resistance. One such process is disclosed in U.S. Pat. No. 3,615,885 to Watson which discloses a procedure for developing thick (up to 0.23 mm) oxide layers on various zirconium alloys. However, this procedure results in significant dimensional changes especially for parts having a thickness below about 5 mm, and the oxide film produced does not exhibit especially high abrasion resistance.

U.S. Pat. No. 2,987,352 to Watson discloses a method of producing a blue-black oxide coating on zirconium alloy parts for the purpose of increasing their abrasion resistance. Both U.S. Pat. No. 2,987,352 and U.S. Pat. No. 3,615,885 produce an oxidized zirconium coating on zirconium alloy by means of air oxidation. U.S. Pat. No. 3,615,885 continues the air oxidation long enough to produce a beige coating of greater thickness than the blue-black coating of U.S. Pat. No. 2,987,352. This beige coating does not have the wear resistance of the blue-black coating and is thus not applicable to many parts where there are two work faces in close proximity. The beige coating wears down more quickly than the blue-black oxide coating with the resulting formation of oxidized zirconium particles and the loss of the integrity of the oxidized zirconium surface. With the loss of the oxide surface the zirconium metal is then exposed to its environment and can lead to transport of zirconium joints away from the surface of the metal into the adjacent environment. U.S. Pat. Nos. 2,987,352 and 3,615,885 are incorporated by reference as though fully disclosed herein.

The blue-black coatings have a thickness which is less than that of the beige coating although the hardness of the blue-black or black coating is higher than that of the beige coating. This harder blue-black oxide coating lends itself better to surfaces such as prosthetic devices. Although the blue-black or black coating is more abrasion resistant than the beige coating it is a relatively thin coating. It is therefore desirable to produce the blue-black coatings of increased abrasion resistance without producing the same type coatings of the prior art.

U.S. Pat. No. 5,037,438 to Davidson discloses a method of producing zirconium alloy prostheses with a oxidized zirconium surface. This specific form of oxidized zirconium, described therein as blue-black or black oxidized zirconium is unique with respect to the excellent thermal conductivity it possesses relative to other conventional prosthetic materials. It combines excellent surface roughness characteristics with very high thermal conductivity. In this way, it possesses the relevant beneficial characteristics of metal and ceramics while avoiding the relevant disadvantages of the former and outperforming the latter. U.S. Pat. No. 5,037,438 is incorporated by reference as though fully set forth herein.

While the introduction of oxidized zirconium for medical implants represented an advance in this area, there was and is room for further refinements. While the durability of the oxidized zirconium implants is excellent compared to conventional materials, it has been recognized that high-integrity oxidized zirconium surfaces have even better durability. A high-integrity oxidized zirconium surface can be produced if the thickness of the oxidized zirconium layer has good uniformity. Non-uniformity of thickness negatively affects durability because it promotes the build-up of internal stresses in the oxide layer and such stresses tend to lead to cracks. Early on in the use of these surfaces for medical implants, uniformity of thickness was not controlled. It has been recognized that controlling uniformity of thickness results in a better oxidized zirconium surface for medical implant applications.

In U.S. Pat. No. 6,447,550, Hunter, et al. described a method for obtaining an oxidized zirconium coating of uniform thickness. Hunter taught that such is obtained by applying pre-oxidation treatment techniques to various zirconium-based materials that result in a refined microstructure and an altered surface roughness. Microstructure refinement is taught in the '550 patent by techniques which include the hot forge conversion of ingot to wrought barstock, closed die forging, rapid solidification, and powder consolidation. The altered surface roughness is accomplished by processes such as grinding, buffing, mass finishing, vibratory finishing, among others. U.S. Pat. No. 6,447,550 is incorporated by reference as though fully set forth herein.

Hunter, et al., in U.S. Pat. No. 6,585,772, provide another method for forming a uniformly thick oxide coating on zirconium or a zirconium alloy. In the method of the '772 patent, Hunter teaches that by inducing an altered surface roughness on a single phase/single composition zirconium based substrate prior to oxidation, control and improvement of the thickness uniformity of the resulting oxidized zirconium layer can be realized. The '772 patent also provides a method for forming a uniformly thick oxide coating on a zirconium or zirconium alloy prosthesis, for implantation in a patient, by inducing an altered surface roughness on at least a portion of the zirconium or zirconium alloy prosthesis, wherein the zirconium or oxidized zirconium consists, at least in part, of a single phase crystalline structure and uniform composition, prior to oxidizing the prosthesis to form a blue-black oxidized zirconium coating of uniform and controlled thickness on at least a portion of the surface of the prosthesis. U.S. Pat. No. 6,585,772 is incorporated by reference as though fully set forth herein.

While both of these techniques of Hunter proved useful in promoting thickness uniformity, the present invention provides yet another distinct method to accomplish the same result. In the present invention, a uniform thickness layer of oxidized zirconium is accomplished using an amorphous zirconium-containing alloy. This represents another technique to produce a surface layer of oxidized zirconium having improved uniformity of thickness and provides another tool in the arsenal of one wishing to fabricate improved medical devices having oxidized zirconium surfaces.

SUMMARY OF THE INVENTION

The invention provides a zirconium or zirconium-containing metal alloy prosthesis or implant coated, at least in part, via in situ oxidation with a uniformly thick blue-black or black layer of oxidized zirconium and a method of forming the aforementioned uniform coating. The uniform coating of oxidized zirconium provides the prosthesis with a thin, dense, low friction, wear resistant, biocompatible surface ideally suited for use on articulating surfaces of joint prostheses wherein a surface or surfaces of the joint articulates, translates, or rotates against mating joint surfaces which are also coated with oxidized zirconium. The uniform oxidized zirconium coating may therefore be usefully employed on the femoral heads or inside surfaces of acetabular cups of hip-joint implants or on the articulating surfaces of other types of prostheses, such as but not limited to knee, shoulder or elbow joints, spinal implants, bone plates and bone screws, etc.

In one embodiment of the present invention, there is a method of producing a uniform coating of blue-black or black oxidized zirconium on a zirconium or zirconium alloy, characterized by the step of oxidizing zirconium having an amorphous structure or a zirconium alloy having an amorphous structure. In some embodiments, the method further comprises the step of altering the surface roughness of said zirconium or zirconium alloy prior to said step of oxidizing. In some embodiments, the step of altering said surface roughness comprises altering to a surface roughness (Ra) in the range of about 3 microinches to about 25 microinches. In some embodiments, the step of altering said surface roughness comprises altering to a surface roughness (Ra) in the range of about 3.5 microinches to about 7 microinches. In some embodiments, the step of altering said surface roughness comprises an abrasive surface preparation process comprising a step selected from the group consisting of grinding, buffing, mass finishing and vibratory finishing and any combination thereof. In some embodiments, the step of oxidizing comprises the use of air as an oxidant. In some embodiments, the step of oxidizing comprises the use of oxygen as an oxidant. In some embodiments, of the method, the zirconium or zirconium alloy comprises about 0.3 percent oxygen by weight.

In another embodiment of the present invention, there is a medical implant characterized by at least one component, said component comprising a substrate comprising zirconium having an amorphous structure or a zirconium alloy having an amorphous structure; a surface layer of blue-black or black oxidized zirconium on at least a portion of said substrate, said surface layer of oxidized zirconium being formed by oxidation of said zirconium or zirconium alloy. In some embodiments, the zirconium or zirconium alloy comprises an altered surface roughness prior to said oxidation. In some embodiments, the altered surface roughness comprises a surface roughness (Ra) in the range of about 3 microinches to about 25 microinches. In some embodiments, the altered surface roughness comprises a surface roughness (Ra) in the range of about 3.5 microinches to about 7 microinches. In some embodiments, the layer of oxidized zirconium is of a thickness of up to about 20 microns. In some embodiments, the layer of oxidized zirconium coating is of a thickness of up to about 10 microns. In some embodiments, the implant portion of the prosthesis body further comprises an irregular surface adapted to accommodate tissue ingrowth on a portion of the prosthesis body. In some embodiments having an irregular surface, the irregular surface is formed of zirconium or zirconium alloy beads attached to the outer surface of the prosthesis body, wherein at least a portion of the surface of the beads is oxidized to blue-black or black oxidized zirconium. In some embodiments having an irregular surface, the irregular surface structure is formed of zirconium or zirconium alloy wire mesh connected to the outer surface of the prosthesis body, wherein at least a portion of the surface of the mesh is oxidized to blue-black or black oxidized zirconium.

In some embodiments having an irregular surface, the irregular surface is a chemically etched surface. In some embodiments having an irregular surface, the irregular surface is plasma spray-deposited surface. In some embodiments having an irregular surface, the irregular surface is a sintered surface. In some embodiments, the medical implant is a vertebral implant. In some embodiments, the medical implant is a dental implant. In some embodiments, the medical implant comprises bone implant hardware. In some embodiments wherein the medical implant comprises bone implant hardware, the bone implant hardware comprises a bone plate or a bone screw.

In some embodiments of the medical implant having at least one component, the medical implant comprises a first component having a bearing surface; and, a second component having a counter-bearing surface adapted to cooperate with the bearing surface of said first component; wherein at least one of said first component or said second component comprises zirconium having an amorphous structure or a zirconium alloy having an amorphous structure; a surface layer of blue-black or black oxidized zirconium on at least a portion of said first component or said second component or both said first and second components, said surface layer of oxidized zirconium being formed by oxidation of said zirconium or zirconium alloy. In some embodiments, the medical implant is a joint prosthesis. In some embodiments having a first component and a second component, the first component comprises a femoral component and said second component comprises an acetabular cup component to form a hip prosthesis. In some embodiments having a first component and a second component, the first component comprises a femoral component which further comprises at least one condyle and said second component comprises a tibial component to form a knee prosthesis. In some embodiments wherein the medical implant is a joint prosthesis, the joint prosthesis is selected from the group consisting of shoulder, ankle, finger, wrist, toe, or elbow prostheses. In some embodiments, the medical implant is a maxillofacial or temporomandibular implant.

In another aspect of the invention, there is provided a substrate comprising zirconium or a zirconium alloy having an amorphous structure; and a surface layer of blue-black or black zirconium on at least a portion of said zirconium or a zirconium alloy. In some embodiments, a portion of the zirconium or zirconium alloy further comprises an altered surface roughness. In other embodiments, the altered surface roughness comprises a surface roughness (Ra) in the range of about 3 microinches to about 25 microinches, or in other embodiments, the range is about 3.5 microinches to about 7 microinches. In some embodiments, the surface layer has a thickness of up to about 20 microns, or in other embodiments, the thickness is up to about 10 microns.

In yet some embodiments, a portion of the surface layer further comprises an irregular surface. In some embodiments, the irregular surface comprises zirconium or zirconium alloy beads attached to the outer surface of the substrate, and wherein at least a portion of the surface of the beads is oxidized to blue-black or black oxidized zirconium. In other embodiments, the irregular surface comprises zirconium or zirconium alloy wire mesh connected to the outer surface of the substrate, wherein at least a portion of the surface of the mesh is oxidized to blue-black or black oxidized zirconium. In yet other embodiments, the irregular surface comprises a chemically etched surface. In other embodiments, the irregular surface comprises a plasma spray-deposited surface. In some other embodiments, the irregular surface comprises a sintered surface.

In some embodiments, the surface layer has a substantially uniform thickness. In some embodiments, the surface layer of zirconium has a thickness in the range of about 3 microns to about 7 microns. In some embodiments, the surface layer of zirconium comprises a polished surface. In other embodiments, the surface layer comprises oxidized zirconium. In some embodiments, the oxidized surface layer is formed by oxidation of said zirconium or zirconium alloy. In some embodiments, the oxidation of the zirconium or zirconium alloy comprises furnace oxidation with oxygen at a temperature in the range of about 900 degrees F. to 1300 degrees F. In other embodiments, the oxidation of the zirconium or zirconium alloy comprises salt-bath oxidation with at least one salt selected from the group consisting of chlorides, nitrates, cyanides, and a combination thereof. In some embodiments, a portion of said zirconium or zirconium alloy further comprises an altered surface roughness prior to said oxidation. In yet another embodiment, the altered surface roughness is formed by subjecting the portion of zirconium or zirconium alloy to an abrasive surface preparation process selected from the group consisting of grinding, buffing, mass finishing, vibratory finishing, and a combination thereof.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION OF THE INVENTION

As used herein, "a" or "an" may mean one or more. As used herein in the claim(s), when used in conjunction with the word "comprising", the words "a" or "an" may mean one or more than one. As used herein, "another" may mean at least a second or more.

As used herein, the term "amorphous" or "amorphous structure" means the condition of lacking long range crystalline order.

As used herein, "zirconium alloy" is defined as any metal alloy containing zirconium in any amount greater than zero. Thus, an alloy in which zirconium is a minor constituent is considered a "zirconium alloy" herein.

The following discussion contains illustrations and examples of preferred embodiments for practicing the present invention. However, they are not limiting examples. Other examples and methods are possible in practicing the present invention.

One aspect of the present invention is to provide a method for forming an oxide coating of uniform thickness on zirconium or a zirconium alloy, using a zirconium which is amorphous or a zirconium alloy which is amorphous. Accordingly, as used throughout herein, the expression "zirconium or zirconium alloy having an amorphous structure" is synonymous with the expression "zirconium having an amorphous structure or a zirconium alloy having an amorphous structure." In a preferred embodiment, an altered surface roughness is induced on the amorphous zirconium or zirconium alloy prior to oxidation. Another aspect of the present invention is to provide a low friction, wear resistant oxide coating of uniform thickness on prosthesis surfaces, such as articulating surfaces and irregular surface structures adapted to accommodate tissue ingrowth on a portion of the prosthesis body.

The subject method of forming an oxide coating of uniform thickness by oxidizing an amorphous zirconium or an amorphous zirconium alloy. Preferably, the method also comprises the step of altering the surface roughness of the amorphous zirconium or zirconium alloy prior to the step of oxidizing. The resulting oxidized zirconium is applicable to variety of medical implant, prosthetic parts, and devices. These prosthetic parts and devices include, but are not limited to, cardiovascular implants including heart valves, total artificial heart implants, ventricular assist devices, vascular grafts and stents; electrical signal carrying devices such as pacemaker and neurological leads, and defibrillator leads; guide wires and catheters; percutaneous devices; and joint prostheses including hip joints or surface replacements, knee joints, shoulder joints, elbows, endoprostheses, spinal segments, and fingers. Illustrative examples of such articulating surfaces are shown in the schematic diagrams, FIGS. 1-4. Additionally, applications are possible in non-articulating implant devices such as bone plates, bone screws, etc.

Figure 2:
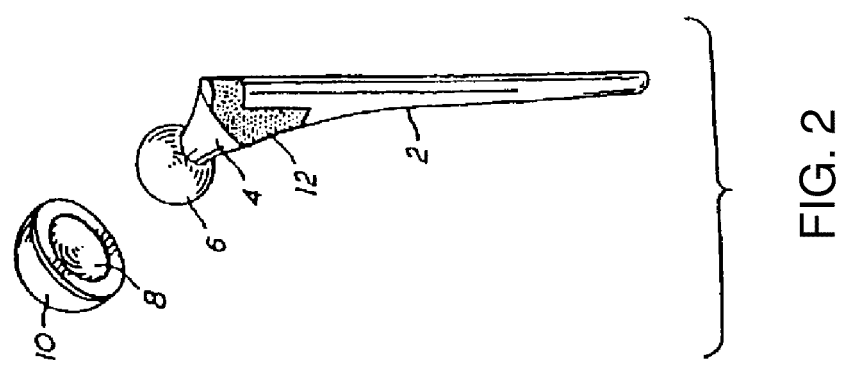
FIG. 2 is a schematic diagram showing a typical hip join prosthesis.
Figure 1:
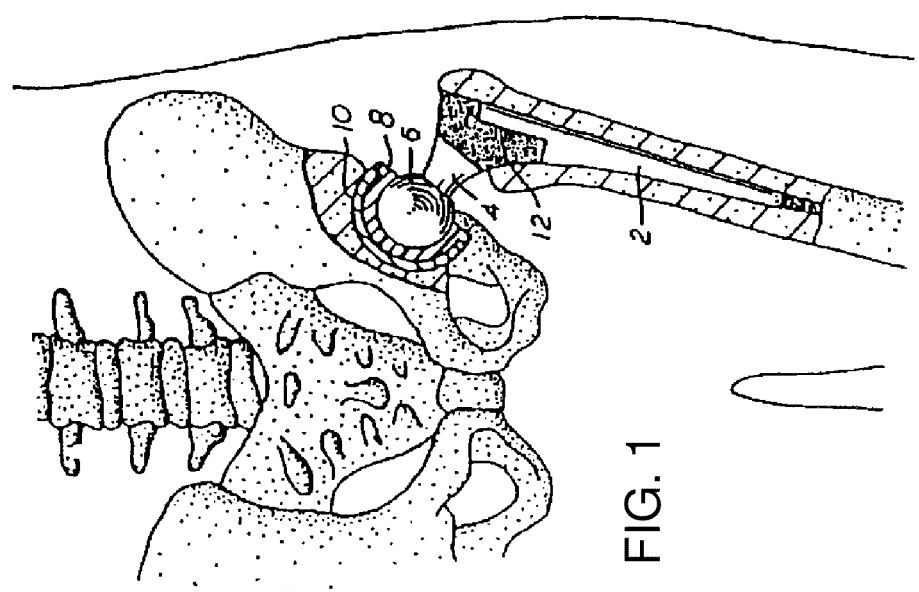
FIG. 1 is a schematic diagram depicting a hip joint prosthesis in position.

A typical hip joint assembly is shown in situ in FIG. 1. FIG. 2 illustrates a typical hip prosthesis prior to implantation, providing details of the individual components. The hip joint stem 2 fits into the femur while the femoral head 6 of the prosthesis fits into and articulates against the inner lining 8 of an acetabular cup 10 which in turn is affixed to the pelvis as shown in FIG. 1. A porous metal bead or wire mesh coating 12 may be incorporated to allow stabilization of the implant by ingrowth of surrounding tissue into the porous coating. Similarly, such a porous metal bead or wire mesh coating can also be applied to the acetabular component. The femoral head 6 may be an integral part of the hip joint stem 2 or may be a separate component mounted upon a conical taper at the end of the neck 4 of the hip joint prosthesis. This allows the fabrication of a prosthesis having a metallic stem and neck but a femoral head of some other material, such as ceramic. This method of construction is often desirable because ceramics have been found to generate less frictional torque and wear when articulating against UHMWPE, the typical lining of the acetabular cup. Additionally, zirconia ceramic has been shown to produce less wear of the UHMWPE than alumina.

Regardless of the materials, however, the femoral head articulates against the inner surface of the acetabular cup thereby causing wear and, in the long term, this may necessitate prosthesis replacement. This is especially the case where the femoral head is of metal and the acetabular cup is lined with an organic polymer or composite thereof. While these polymeric surfaces provide good, relatively low friction surfaces and are biocompatible, they are subject to wear and accelerated creep due to the frictional heat and torque to which they are subjected during ordinary use.

Figure 4:
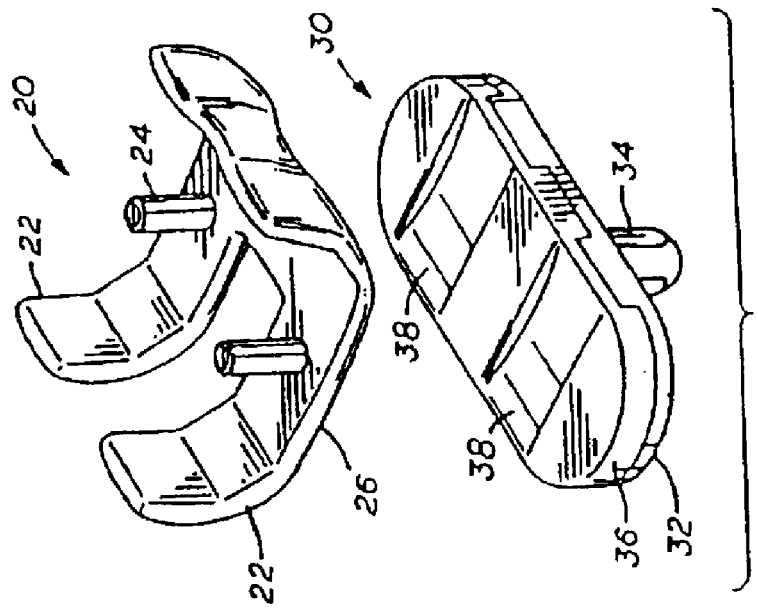
FIG. 4 is a schematic diagram of the parts of a typical knee joint.
Figure 3:
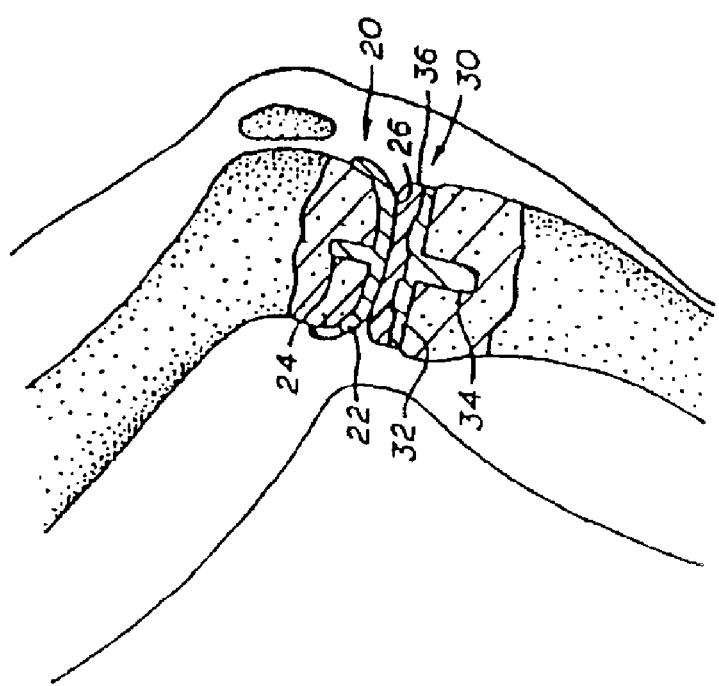
FIG. 3 is a schematic diagram of a knee joint prosthesis in place.

While UHMWPE that has been cross-linked through irradiation followed by a heating step has been shown to exhibit greater wear resistance, it has similar shortcomings. A typical knee joint prosthesis is shown in situ in FIG. 3. FIG. 4 illustrates a typical knee prosthesis prior to implantation, providing details of the individual components. The knee joint includes a femoral component 20 and a tibial component 30. The femoral component includes condyles 22 which provide the articulating surface of the femoral component and pegs 24 for affixing the femoral component to the femur. The tibial component 30 includes a tibial base 32 with a peg 34 for mounting the tibial base onto the tibia. A tibia platform 36 is mounted atop the tibial base 32 and is supplied with grooves 38 similar to the shape of the condyles 22. The bottom surfaces of the condyles 26 contact the tibial platform's grooves 38 so that the condyles articulate within these grooves against the tibial platform. While condyles are typically fabricated of metals, the tibial platform may be made from an organic polymer or a polymer-based composite. Thus, the hard metallic condyle surfaces 26 would articulate against a relatively softer organic composition. This may result in wear of the organic material, i.e. the tibial platform, necessitating the replacement of the prosthesis. As in the case of the hip joint, porous bead or wire mesh coatings can also be applied to either the tibial or femoral components of the knee or both.

The invention provides uniformly thick oxidized zirconium coated orthopedic implants or prostheses fabricated of zirconium or zirconium containing metal alloys or a thin coating of zirconium or zirconium alloy on conventional orthopedic implant materials. Uniformity of thickness is desirable to insure that the characteristics and properties of the layer of oxidized zirconium are relatively constant over the surface of the prosthetic device. In order to form continuous and useful oxidized zirconium coatings of uniform thickness over the desired surface of the metal alloy prosthesis substrate, the metal alloy preferably contains from about 80 to about 100 wt % zirconium, preferably from about 94 to about 100 wt %. Oxygen, and other common alloying elements may be used in the alloy. For example, in one preferred embodiment, the zirconium or zirconium alloy is about 0.3% by weight of oxygen.

Although not wishing to be bound to theory, it is believed that an amorphous zirconium or zirconium alloy is useful in the present invention because the lack of crystallinity necessarily eliminates grain boundaries in the material. The simplest repeating unit in a crystalline material is the unit cell. Unit cell crystals form colonies (dendrites). As solidification nears completion, the dendrites contact one another. These area of contacts are grain boundaries. In the oxidative process that forms the oxidized zirconium coating, the rate of oxidation is modified at grain boundaries relative to the rate in the bulk of the material. Eliminating or minimizing grain boundaries thereby minimizes channeling of oxidation through grain boundaries, resulting in non-uniformity of thickness of the resulting layer of oxidized zirconium. Optionally, altering the surface roughness of the amorphous zirconium or zirconium alloy serves to further enhance thickness uniformity and, as a result, oxide integrity. Again not wishing to be bound by theory, it is believed that roughening the surface to the values described herein increases the number of initiation sites for oxidation, resulting in uniform growth of the oxidation layer inward toward the substrate.

The base amorphous zirconium or zirconium containing metal alloys are fabricated by conventional methods to the shape and size desired to obtain a prosthesis substrate. In the preferred embodiment, the substrate amorphous zirconium or zirconium alloy is subjected to an abrasive surface preparation process prior to oxidation that includes, but is not limited to, grinding, buffing, mass finishing and vibratory finishing. The abrasive surface preparation process is used to induce an altered surface roughness (Ra) of from about 3 microinches to about 25 microinches. Alternatively, the range of surface roughness can be from about 3.5 to about 7 microinches. The appropriate altered surface roughness is induced by altering the pre-existing surface roughness to an altered surface roughness of such a magnitude as to permit the formation of a uniform oxide coating when the amorphous zirconium or zirconium alloy is subjected to the prescribed oxidation process.

The substrate is then subjected to process conditions which cause the natural (in situ) formation of a tightly adhered, diffusion-bonded coating of uniformly thick oxidized zirconium on its surface. The process conditions include, for instance, air, steam, or water oxidation or oxidation in a salt bath. These processes ideally provide a thin, hard, dense, blue-black or black, low-friction wear-resistant uniformly thick oxidized zirconium film or coating of thicknesses typically on the order of several microns on the surface of the prosthesis substrate. Below this coating, diffused oxygen from the oxidation process increases the hardness and strength of the underlying substrate metal.

The air, steam and water oxidation processes are described in now-expired U.S. Pat. No. 2,987,352 to Watson, the teachings of which are incorporated by reference as though fully set forth. The oxidation process applied to an amorphous zirconium or zirconium alloy, preferably having an altered surface roughness, provides a firmly adherent black or blue-black layer of uniformly thick oxidized zirconium. If the oxidation is continued to excess, the coating will whiten and separate from the metal substrate. For convenience, the metal prosthesis substrate may be placed in a furnace having an oxygen-containing atmosphere (such as air) and typically heated at 900°-1300° F. for up to about 6 hours. However, other combinations of temperature and time are possible. When higher temperatures are employed, the oxidation time should be reduced to avoid the formation of the white oxide.

One of the salt-bath methods that can be used to apply the oxidized zirconium coatings to the metal alloy prosthesis, is the method of U.S. Pat. No. 4,671,824 to Haygarth, the teachings of which are incorporated by reference as though fully set forth. The salt-bath method provides a similar, slightly more abrasion resistant blue-black or black oxidized zirconium coating. This method requires the presence of an oxidation compound capable of oxidizing zirconium in a molten salt bath. The molten salts include chlorides, nitrates, cyanides, and the like. The oxidation compound, sodium carbonate, is present in small quantities, up to about 5 wt %. The addition of sodium carbonate lowers the melting point of the salt. As in air oxidation, the rate of oxidation is proportional to the temperature of the molten salt bath and the '824 patent prefers the range of 550°-800° C. (1022°-1470° F.). However, the lower oxygen levels in the bath produce thinner coatings than for furnace air oxidation at the same time and temperature. A salt bath treatment at 1290° F. for four hours produces an oxide coating thickness of roughly 7 microns.

The overall thickness of the oxidized zirconium coating is primarily controlled by the variables of time and temperature of the in-situ growth process. The instant invention is concerned with the uniformity of thickness of the coating so created. Creation of a uniform oxide coating during the oxidation process, by the here claimed method, is dependent on both a surface with appropriate altered surface roughness and amorphous composition. The oxide coating initiates and grows from surface asperities, so the oxide initiation sites may be spaced too far apart to produce a uniform coating thickness on a surface that is too smooth. The oxide layer grows by oxygen diffusion along grain boundaries and through microstructural grains. The oxidation rate can be different in grains of different structure and composition. Thus, the oxide coating may not grow with a uniform thickness through a heterogeneous microstructure. Although, specific limits for the necessary minimum surface roughness can be alloy and application dependent, sufficient phase homogeneity may be achieved through the use of an amorphous zirconium metal or amorphous zirconium alloy.

The uniformly thick oxidized zirconium coating may range up to about 20 microns. It is preferred that a uniformly thick blue-black oxidized zirconium layer ranging in thickness from about 1 to about 10 microns should be formed. It is most preferred that the uniformly thick oxidized zirconium layer range from about 3 microns to about 7 microns. For example, furnace air oxidation at 1100° F. for 3 hours will form a uniform oxide coating of a thickness of 4-5 microns on a zirconium alloy having greater than 96 wt % zirconium with a surface roughness (Ra) of about 4 microinches. Longer oxidation times and higher oxidation temperatures will increase this thickness, but may compromise coating integrity. Thicknesses of up to 20 microns or greater can be achieved under appropriate conditions. For example, one hour at 1300° F. will form an oxide coating thickness of about 9 microns. Of course, because only a thin oxide is necessary on the surface, only very small dimensional changes, typically less than 10 microns over the thickness of the prosthesis, will result. In general, thinner coatings (1-10 microns) have better attachment strength. However, depending upon the application coatings of greater thickness may be used.

Blue-black or black oxidized zirconium coatings produced by any of the prior art methods are quite similar in hardness. For example, if the surface of a wrought zirconium alloy prosthesis substrate is oxidized, the hardness of the surface shows a dramatic increase over the 200 Knoop hardness of the original metal surface. The surface hardness of the blue-black oxidized zirconium surface following oxidation by either salt bath or air oxidation process is approximately 1200-1700 Knoop hardness.

The diffusion-bonded, low friction, highly wear resistant, uniformly thick oxidized zirconium coatings of the present invention can be applied to the surfaces of orthopedic implants subject to conditions of wear and to prosthetic implants and devices requiring a biocompatible surface. Such surfaces include, but are not limited to, the articulating surfaces of knee joints, elbows and hip joints. In the case of hip prostheses (FIGS. 1 and 2), the femoral head 6 is an example of where the oxidized zirconium coating may be located. In such prostheses, the femoral head and stem are typically fabricated of metal alloys while the acetabular cup may be fabricated from ceramics, metals or organic polymer-lined metals or ceramics. However, any other portions of the prostheses may have the oxidized zirconium coating of the present invention. In the case of knee prostheses (FIGS. 3 and 4), the condyle surface 26 is an example of where the oxidized zirconium coating may be located. However, any other portions of the prostheses may have the oxidized zirconium coating of the present invention.

When the oxidized zirconium coatings are applied to surfaces subject to wear, it is desirable to obtain a smooth finished surface to minimize abrasive wear. After the oxidation process, the oxide coating surface can be polished by any of a variety of conventional finishing techniques. Sufficient oxide thickness must be produced to accommodate the chosen finishing technique. For example, a surface with a uniform oxide coating of about 5 microns thick that had a pre-oxidation surface roughness (Ra) of about 4 microinches can be burnished to a final surface roughness (Ra) of about 2 microinches with a loss of about 1 micron in oxide thickness.

In the medical implants fabricated using the invention described herein, it is sometimes desirable to have a textured surface to promote bone in-growth and on-growth. A number of techniques, known to those of ordinary skill in the art may be combined with the teachings of the present invention to fabricate such medical implants. Zirconium or zirconium alloy can also be used to provide a porous bead or wire mesh surface to which surrounding bone or other tissue may integrate to stabilize the prosthesis. These porous coatings can be treated simultaneously by the oxidation of the base prosthesis for the elimination or reduction of metal ion release. Furthermore, zirconium or zirconium alloy can also be used as a surface layer applied over conventional implant materials prior to inducing an altered surface roughness, in situ oxidation and formation of the uniform oxidized zirconium coating. Other applicable means to achieve a textured surface, also known to those of ordinary skill in the art include chemical etching, various deposition methods such as chemical vapor deposition, plasma-spray deposition, etc., as well as others.

The process of the present invention provides another avenue to avoid the problems of formation of thick oxide coatings of low abrasion resistance and of significant dimensional changes of the process in U.S. Pat. No. 3,615,885. The control of both overall coating thickness and the uniformity of the thickness affords a great deal of dimensional control in the fabrication of prosthetic devices wherein exacting tolerances are required. The present invention also produces an oxide film that is highly abrasion resistant, unlike that of the '885 patent.

The process of the present invention, by oxidizing an amorphous zirconium or zirconium alloy, preferably following a step of inducing an altered surface roughness on the amorphous zirconium or zirconium alloy, results in the formation of a blue-black oxidized zirconium coating of uniform thickness, the depth of which can be controlled by the proper choice of the oxidation conditions. The formation of a uniformly thick oxide coating provides an oxide coating of variable and controlled thickness with especially high abrasion resistance and reduced wear due to high integrity of the adhesion between the oxide layer and the underlying zirconium or zirconium alloy and the high integrity of the adhesion within the oxide layer. The term "high integrity" denotes an oxide coating that is uniform in thickness with no visible cracks or pores when viewed in cross-section by optical microscopy.

The invention provides an amorphous zirconium or zirconium-containing metal alloy prosthesis coated via in situ oxidation with a coating of oxidized zirconium of uniform thickness. The uniformly thick oxidized zirconium coating provides the invention prosthesis with a thin, dense, low friction, high integrity, wear resistant biocompatible surface ideally suited for use on articulating surfaces of joint prosthesis wherein a surface or surfaces of the joint articulates, translates or rotates against mating joint surfaces. The uniformly thick oxidized zirconium coating may therefore be usefully employed in joint prostheses such as on the femoral heads or inside surfaces of acetabular cups of hip-joint implants or on the articulating surfaces of other types of prostheses, such as knee joints. Generally, such implants can be described as multi-component prostheses comprising a first component having a bearing surface and a second component having a counter-bearing surface, where at least one of the components comprises zirconium or a zirconium alloy having an amorphous structure and where a surface layer of blue-black or black oxidized zirconium exists on at least a portion of a component comprising zirconium or a zirconium alloy, the surface layer of oxidized zirconium being formed by oxidation of said zirconium or zirconium alloy. Alternatively, other implants amenable to the present invention are those having at least one component having a substrate comprising amorphous zirconium or an amorphous zirconium alloy; a surface layer of blue-black or black oxidized zirconium on at least a portion of the substrate; the surface layer of oxidized zirconium being formed by oxidation of the zirconium or zirconium alloy. The present invention is applicable to any prostheses, including shoulder, ankle, finger, wrist, toe, elbow, or other prostheses. Other possible applications include maxillofacial or temporomandibular implants. Other implants such as dental and vertebral implants could be fabricated with uniform thickness oxidized zirconium surfaces according to the present invention. It is also applicable to implant hardware, such as bone plates and bone screws. Other possibilities are clear to one of ordinary skill in the art.

When a joint surface coated with a uniformly thick oxidized zirconium is employed in a manner wherein it articulates or rotates against a non-metallic or non-oxidized zirconium coated surface, the low friction characteristic and high integrity of the uniformly thick coating causes reduced friction, wear, and heat generation relative to prior art prostheses. This reduced heat generation results in a lowered tendency for the non-metallic or non-oxidized zirconium coating bearing surface to experience creep and torque so that the useful life of the opposing surface is enhanced. Organic polymers, such as UHMWPE, exhibit rapidly increased rates of creep when subjected to heat with consequent deleterious effect on the life span of the liner. Wear debris of the polymer leads to adverse tissue response and loosening of the device. Thus, not only does the uniformly thick oxidized zirconium coating serve to improve the protection of the prosthesis substrate to which it is applied due to its high integrity, it also, as a result of its low friction surface, protects those surfaces against which it is in operable contact and consequently enhances the performance and life of the prosthesis.

A uniformly thick oxidized zirconium coated joint surface also enhances the useful life of the opposing surface when the opposing surface is body tissue. The surgical replacement of one component of the joint is termed "hemiarthroplasty" and because the repaired joint has only one artificial (prosthesis) component, the artificial component is often termed a "unipolar" prosthesis, or "endoprosthesis." The uniformly thick oxidized zirconium coating is a low friction surface for articulation, translation and rotation against body tissue thereby having the same beneficial effect for a body tissue counterface as it does for an organic polymer counterface.

The usefulness of oxidized zirconium coated prosthesis is not limited to load bearing prostheses, especially joints, where a high rate of wear may be encountered. Other applications are possible in non-articulating implant devices such as bone plates, bone screws, etc. Because the uniformly thick oxidized zirconium coating is firmly bonded to the zirconium alloy prosthesis substrate, it provides an enhanced barrier between the body fluids and the zirconium alloy metal thereby preventing the corrosion of the alloy by the process of ionization and its associated metal ion release compared to non-uniform oxide coatings.

Additionally, the natural in situ formation of a uniformly thick oxidized zirconium coating from the presence of zirconium in the substrate metal involves oxygen diffusion into the metal substrate below the oxide coating. Oxygen, an alloying constituent in zirconium, increases the strength of the metal substrate, particularly the fatigue strength. A preferred embodiment is one having a zirconium or zirconium alloy with an oxygen content of about 0.3% (w/w). Furthermore, the high integrity of the uniformly thick coating reduces the number of fatigue crack initiation sits relative to a non-uniformly thick oxide coating that contains cracks or pores. Resistance to fatigue loading is paramount in many orthopedic implant applications such as the hip stem, and femoral and tibial knee components. Thus, not only does the formation of the uniformly thick oxidized zirconium coating improve wear, fiction, and corrosion resistance, it also improves the mechanical integrity of the implant device from a strength standpoint.

Figure 5:
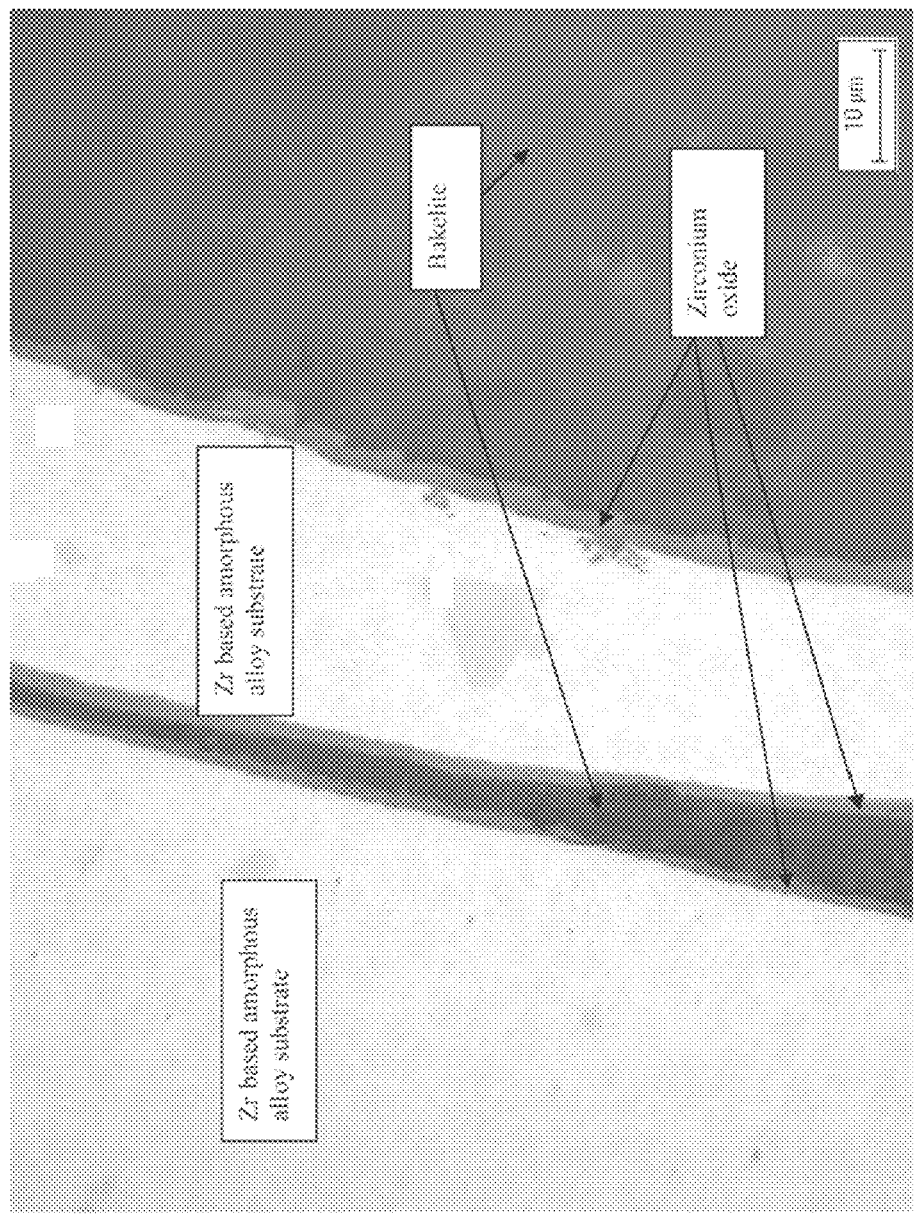
FIG. 5 shows a sample of zirconium alloy mounted on Bakelite after oxidation for 1 hour at 630° C.
Figure 6:
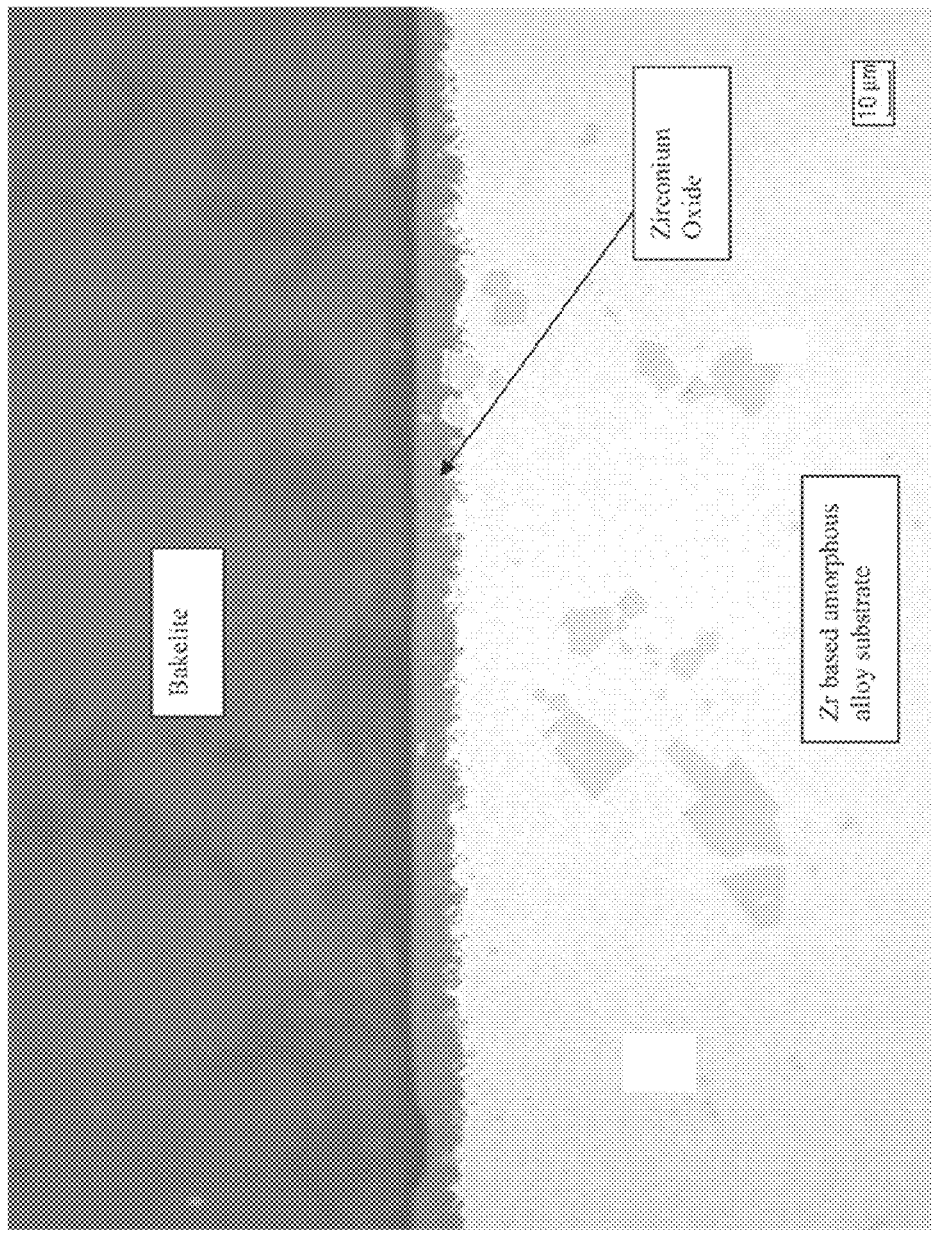
FIG. 6 shows a sample mounted on Bakelite after oxidation for 3 hours at 630° C.

An amorphous alloy of Zr—Ti—Cu—Ni—Be with Zr as the major alloying constituent (55%) demonstrates the usefulness of the present invention. Samples were oxidized at 630° C. for 1 and 3 hours. The thickness of the oxidized zirconium layer was measured by preparing the sample for metallographic inspection. The metallographic images of the oxidized samples are shown in FIGS. 5 (1 hour oxidation) and 6 (3 hour oxidation). The average oxide thickness (±standard deviation) after 1 hour of oxidation was 1.5±0.4 μm whereas after 3 hours it was 8.9±0.7 μm. FIG. 5 shows a cracked sample of zirconium alloy mounted on Bakelite after oxidation for 1 hour at 630° C. FIG. 6 shows a sample mounted on Bakelite after oxidation for 3 hours at 630° C. In each case, the zirconium-based amorphous alloy substrate material is shown with an oxidized zirconium layer. The thickness of the layer formed after 1 hour of oxidation had a coefficient of variation of 26.6%, while the thickness of the layer formed after 3 hours of oxidation had a coefficient of variation of 7.9%. The energy dispersive x-ray analysis of the oxide surface showed that it is mainly composed of oxidized zirconium.

Thus, a 3 hour oxidation using the method of the present invention had a coefficient of variation of about 8%. This result is comparable to the method of Hunter et al (U.S. Pat. No. 6,447,550) using pre-oxidation treatment techniques that result in a refined microstructure and an altered surface roughness. An 18% coefficient of variation in the uniformity of thickness of the oxidized zirconium is obtained using the methodology of the '550 patent in which an as-cast material had a roughened surface having an Ra value of 4-8 microinches. When the as-cast material was replaced with a wrought (refined grain size) material, the variation dropped to 6% when the surface was roughened to an Ra value of 4-8 microinches. In comparison, the conventional method of forming surface layers of oxidized zirconium, as described in U.S. Pat. No. 5,037,438, yields a surface layer thickness with a coefficient of variation of 72%. Thus, the use of the present invention affords a new way to form an oxidized zirconium surface layer having uniform thickness.

Although the invention has been described with reference to its preferred embodiments, those of ordinary skill in the art many, upon reading this disclosure, appreciate changes and modifications which may be made and which do not depart from the scope and spirit of the invention as described above or claimed hereafter.

All patents and publications mentioned in the specification are indicative of the level of those skilled in the art to which the invention pertains. All patents and publications are herein incorporated by reference to the same extent as if each individual publication was specifically and individually indicated to be incorporated by reference.

One skilled in the art readily appreciates that the present invention is well adapted to carry out the objectives and obtain the ends and advantages mentioned as well as those inherent therein. Systems, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the claims.

What is claimed is:

1. A substrate comprising:
   a zirconium or a zirconium alloy having an amorphous structure; and
   a surface layer of blue-black or black zirconium oxide on at least a portion of said zirconium or a zirconium alloy, wherein said surface layer has a substantially uniform thickness.

2. The substrate of claim 1, wherein a portion of said zirconium or zirconium alloy further comprises an altered surface roughness.

3. The substrate of claim 2, wherein said altered surface roughness comprises a surface roughness (Ra) in the range of about 3 microinches to about 25 microinches.

4. The substrate of claim 3, wherein said altered surface roughness comprises a surface roughness (Ra) in the range of about 3.5 microinches to about 7 microinches.

5. The substrate of claim 1, wherein said surface layer has a thickness of up to about 20 microns.

6. The substrate of claim 1, wherein said surface layer has a thickness of up to about 10 microns.

7. The substrate of claim 1, wherein a portion of the surface layer further comprises an irregular surface.

8. The substrate of claim 7, wherein said irregular surface comprises zirconium or zirconium alloy beads attached to the outer surface of the substrate, and wherein at least a portion of the surface of the beads is oxidized to said blue-black or black zirconium oxide surface layer.

9. The substrate of claim 7, wherein said irregular surface comprises a chemically etched surface.

10. The substrate of claim 7, wherein said irregular surface comprises a plasma spray-deposited surface.

11. The substrate of claim 7, wherein said irregular surface comprises a sintered surface.

12. The substrate of claim 7, wherein said irregular surface comprises zirconium or zirconium alloy wire mesh connected to the outer surface of the substrate, wherein at least a portion of the surface of the mesh is oxidized to said blue-black or black zirconium oxide surface layer.

13. The substrate of claim 1, wherein said surface layer of zirconium oxide has a thickness in the range of about 3 microns to about 7 microns.

14. The substrate of claim 1, wherein said surface layer of zirconium oxide comprises a polished surface.

15. The substrate of claim 1, wherein said surface layer comprises oxidized zirconium.

16. The substrate of claim 15, wherein said oxidized surface layer is formed by oxidation of said zirconium or zirconium alloy.

17. The substrate of claim 16, wherein said oxidation of the zirconium or zirconium alloy comprises furnace oxidation with oxygen at a temperature in the range of about 900 degrees F. to 1300 degrees F.

18. The substrate of claim 15, wherein a portion of said zirconium or zirconium alloy further comprises an altered surface roughness prior to said oxidation.

19. The substrate of claim 18, wherein said altered surface roughness is formed by subjecting said portion of zirconium or zirconium alloy to an abrasive surface preparation process selected from the group consisting of grinding, buffing, mass finishing, vibratory finishing, and a combination thereof.

20. The substrate of claim 1, wherein said oxidation of the zirconium or zirconium alloy comprises salt-bath oxidation with at least one salt selected from the group consisting of chlorides, nitrates, cyanides, and a combination thereof.

* * * * *